United States Patent
Biehler

(10) Patent No.: US 10,010,378 B2
(45) Date of Patent: Jul. 3, 2018

(54) RAPID SEQUENCE MEDICAL PROCEDURE TRAY

(71) Applicant: Variety Children's Hospital, Miami, FL (US)

(72) Inventor: Jefry Biehler, Miami, FL (US)

(73) Assignee: Variety Children's Hospital, Miami, FL (US)

(*) Notice: Subject to any disclaimer, the term of this patent is extended or adjusted under 35 U.S.C. 154(b) by 376 days.

(21) Appl. No.: 14/819,691

(22) Filed: Aug. 6, 2015

(65) Prior Publication Data
US 2017/0035512 A1 Feb. 9, 2017

(51) Int. Cl.
*B65D 83/04* (2006.01)
*A61B 50/30* (2016.01)
*A61B 50/00* (2016.01)
*A61B 50/33* (2016.01)

(52) U.S. Cl.
CPC .......... *A61B 50/3001* (2016.02); *A61B 50/00* (2016.02); *A61B 50/33* (2016.02); *A61B 2050/3008* (2016.02)

(58) Field of Classification Search
CPC .............. B65D 25/205; A61B 50/33; A61B 2050/3008; A61B 50/3001
USPC .... 206/232, 438, 459.5, 528, 534, 538–540, 206/561, 570–572; 40/299.01; 283/62, 283/900
See application file for complete search history.

(56) References Cited

U.S. PATENT DOCUMENTS

| | | | | |
|---|---|---|---|---|
| 4,039,080 A | * | 8/1977 | Cappuccilli | A61J 7/0084 206/538 |
| 5,223,220 A | * | 6/1993 | Fan | B01L 3/5023 206/570 |
| 5,379,887 A | * | 1/1995 | Conley, Jr. | B25H 3/02 206/459.5 |
| 5,431,450 A | * | 7/1995 | Coleman | B42D 15/0046 283/900 |
| 5,791,478 A | * | 8/1998 | Kalvelage | A61J 1/035 206/531 |
| 6,652,047 B1 | * | 11/2003 | Maguire, Jr. | A61J 7/04 206/534 |
| 2004/0251165 A1 | * | 12/2004 | Girzaitis | A61J 7/04 206/534 |
| 2010/0282635 A1 | * | 11/2010 | Murphy | A47B 88/90 206/561 |
| 2013/0062245 A1 | * | 3/2013 | Folchini | A61M 5/002 206/571 |
| 2015/0366753 A1 | * | 12/2015 | Ryan | A61J 1/03 206/570 |

* cited by examiner

*Primary Examiner* — Luan K Bui
(74) *Attorney, Agent, or Firm* — Saliwanchik, Lloyd & Eisenschenk

(57) ABSTRACT

The subject invention provides a rapid sequence intubation tray that enables fast and accurate medication dosing of patients under emergency conditions. By "automating" medication dosing, the subject invention reduces delays in medication administration and reduces the risk of medication errors.

16 Claims, 3 Drawing Sheets

RAPID SEQUENCE MEDICAL PROCEDURE TRAY

BACKGROUND OF INVENTION

Medical emergencies require fast and patient-specific care. Endotracheal intubation, for example, is one emergency procedure that requires a series of multiple injections, which must occur within the time frame of seconds to avoid possibly permanent injury. Although emergency room personnel is generally well trained to perform emergency procedures, the treatment of children poses special challenges because children require adjustments of medication dosages to their body weight. Hospitals and other health care providers are often prepared for adult emergency patients, but many are ill-prepared for the added complexity of weight-based calculations in medication dosages required for children, especially during urgent situations. Errors, delays, and deviations from recommended standards for adult patients can adversely impact outcome in pediatric emergencies. It is common for emergency departments, even those caring primarily for adults, to maintain pediatric supplies and medications as a contingency. However, maintaining competencies to be able to appropriately treat children during emergencies is challenging and not every emergency department has a pediatric emergency physician on call. Such situations lend themselves to errors and delays, both of which can have disastrous consequences to patients, their families and society.

Exact dosing of medications in emergency situations is especially challenging when treating low-weight children including full-term and premature babies. Calculations of exact dosages or determination of dosages from dosing tables are time-consuming and potential sources for medication errors. Endotracheal intubations require the performance of a series of injections of medications within seconds, and a device that can reduce the time needed to administer medications and reduce the possibility for error can have broad impact on favorable patient outcome. The subject invention provides such a device that moves medication dosage determination and preparation time out of the emergency situation and provides ready-to-use medication trays suitable for patients of a wide range of body weights for safe rapid sequence intubations.

BRIEF SUMMARY

The subject invention provides rapid sequence medical procedure trays that enable fast and accurate medication dosing of patients during performance of emergency procedures.

In one embodiment, a device include: a tray having a plurality of parallel compartments holding medication receptacles and a single compartment perpendicular to the plurality of parallel compartments. The single compartment can include: a label covering a surface of the single perpendicular compartment and displaying a patient weight and a purpose of use, wherein the label comprises sections suitably aligned with a single parallel compartment; and a plurality of indications displayed in the label sections, wherein the indications comprise a medication name and a medication volume, wherein the medication volume is calculated based on the patient weight indication displayed on said label.

DETAILED DISCLOSURE

The subject invention provides a rapid sequence medical procedure tray that enables fast and accurate medication dosing of patients during performance of emergency procedures. The device of the subject invention "automates" medication dosing and thereby reduces the risk of medication errors. The skilled artisan can appreciate that patient weight-based dosing of medications is especially critical in children and babies, and most critical in newborn and/or premature babies. The subject invention provides a device that obviates the calculation of medication dosages based on patient weight under emergency conditions by providing a combination of pre-apportioned medication receptacles and pre-calculated medication volumes based on patient weight to allow rapid sequence medication administration during emergency procedures with reduced risk of medication errors.

In embodiments of the subject invention, the device comprises a rapid sequence medical procedure tray holding a plurality of pre-apportioned medications commonly used in a specific emergency procedure and the entirety of information needed by an emergency care provider to administer the correct dosages of the pre-apportioned medications to a patient based on the patient's body weight.

In preferred embodiments, the subject invention provides an error-reducing patient dosing tool for use during the performance of emergency procedures, including, for example, endotracheal intubations. In more preferred embodiments, the subject invention provides an error-reducing patient dosing tool for use in pediatric patients. In most preferred embodiments, the subject invention provides an error-reducing patient dosing tool for endotracheal intubation of pediatric patients.

Figure 1:
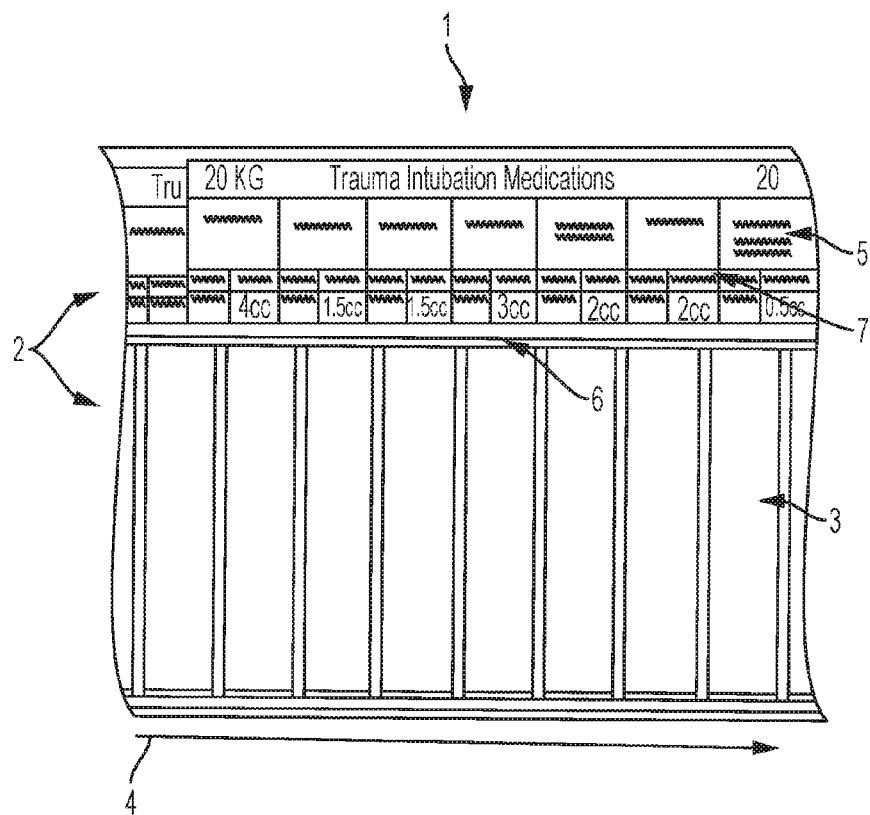
FIG. 1 is a photograph of the top view of a rapid sequence intubation tray comprising a plurality of parallel compartments for medication receptacles and a label for the patient weight of 20 kilogram (kg) positioned in the single large compartment.
Figure 3:
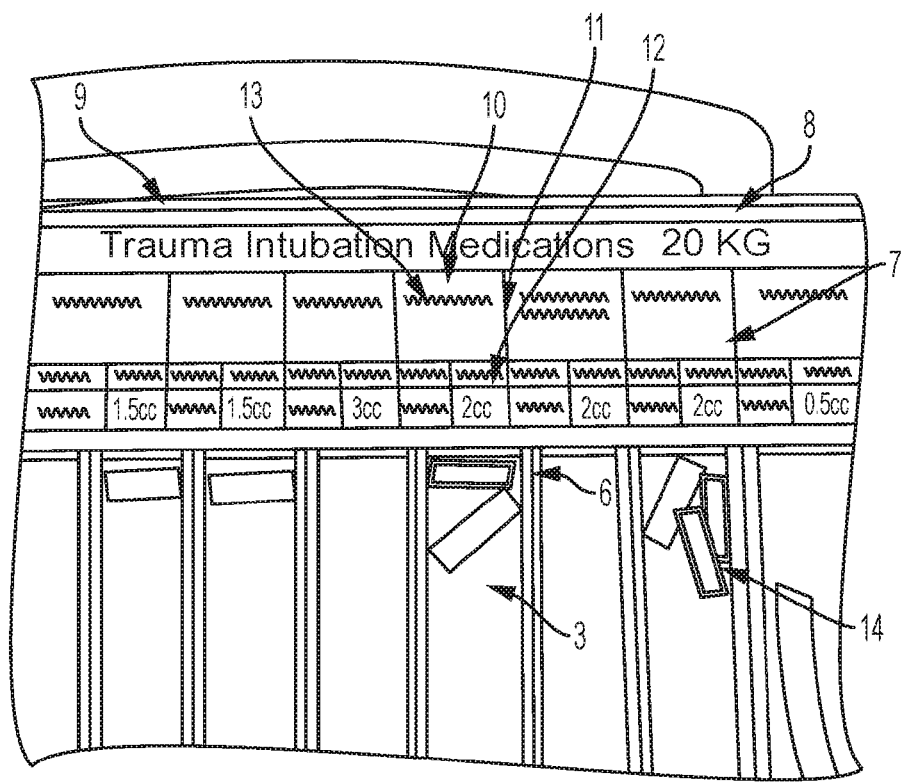
FIG. 3 is a photograph of the top view of a rapid sequence intubation tray a plurality of parallel compartments for medication receptacles, a single label in the single large compartment and a plurality of small labels to be attached to medication receptacles in the plurality of parallel small compartments.

As illustrated in FIGS. 1 and 3, which show certain embodiments of the subject invention, the subject invention comprises a tray having a rectangular shape 1 and a plurality of compartments 2. In some embodiments, the tray is manufactured from an inert material such as plastic. In other embodiments the tray is manufactured from any durable material including, but not limited to rubber, metal, or glass. In preferred embodiments, the tray is manufactured from a material that can withstand sterilization.

As shown in one embodiment in FIG. 1, the majority of compartments 3 of the tray are aligned parallel to each other and perpendicular to the longitudinal axis 4 of the tray. The number of parallel compartments 3 can vary. In certain embodiments, the tray 1 of the subject invention includes as few as 2 compartments, in other embodiments the tray includes up to 50 compartments, or any number in between. In preferred embodiments, the tray comprises less than 20 parallel compartments.

In certain embodiments of the subject invention, the parallel compartments 3 are of the same width. In other embodiments, the parallel compartments 3 are of different widths. In preferred embodiments, the parallel compartments 3 are of sufficient width to house a plurality of medication-containing receptacles. In some embodiments, each medication is contained in a single receptacle, with each single receptacle housed in a single parallel compartment 3. In other embodiments, each medication is apportioned into multiple receptacles, which multiple receptacles are housed within a single parallel compartment 3.

In preferred embodiments, the tray 1 of the subject invention comprises a single large compartment 5 which is aligned with the longitudinal axis 4 of the tray. As illustrated in FIG. 3, the single large compartment 5 is perpendicular to the plurality of parallel compartments 3 so as to share a wall 6 with each parallel compartment 3. In one embodiment, the single large compartment 5 occupies less than half of the tray surface. In other embodiments, the single large compartment 5 occupies more than half of the tray surface. The skilled artisan will appreciate that the size of the single large compartment 5 and the size of the plurality of parallel compartments 3 can vary according to the size and number of receptacles housed in the parallel compartments 3.

Figure 2:
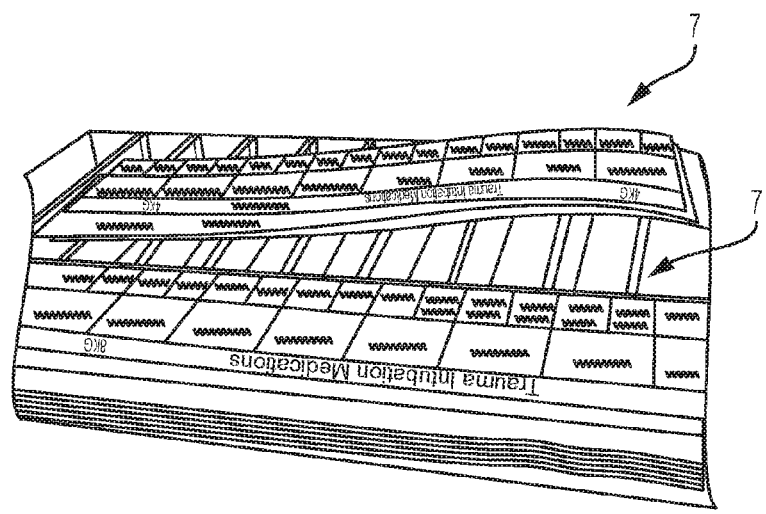
FIG. 2 is a photograph of several color-coded labels for several different patient weights.

In most embodiments, the subject invention comprises a label 7 which is sized as to suitably be placed into the single large compartment 5. In most embodiments, the label 7 covers the entire surface of the single large compartment 5. In preferred embodiments and as illustrated in FIG. 2, the subject invention provides a plurality of labels 7, which can be interchangeably placed into the single large compartment 5. The labels 7 of the subject invention can be manufactured from any material suitable to display letters and numbers. In preferable embodiments, the labels are manufactured from plastic.

In embodiments of the subject invention and as illustrated in FIG. 3, each label 7 displays a single weight indication 8 and a single indication of purpose or use 9 of the tray. In most preferred embodiments, each label 7 comprises a prominent indication of the weight of a patient in kilograms or pounds 8 and the letters "Trauma Intubation Medications" 9 as indication of purpose or use of the tray. In further preferred embodiments, the weight indication 8 and indication of purpose or use 9 are displayed in large fonts in white or a light color on a black or dark background or, alternatively, in black or dark color on a white or light background.

In most embodiments of the subject invention, the label is partitioned into a plurality of sections 10. In preferred embodiments, the borders 11 marking the outline of each label section 10 are suitably aligned with the walls 6 of the parallel compartments 3 in such a way that one label section 10 is aligned with one parallel compartment 3.

Figure 4:
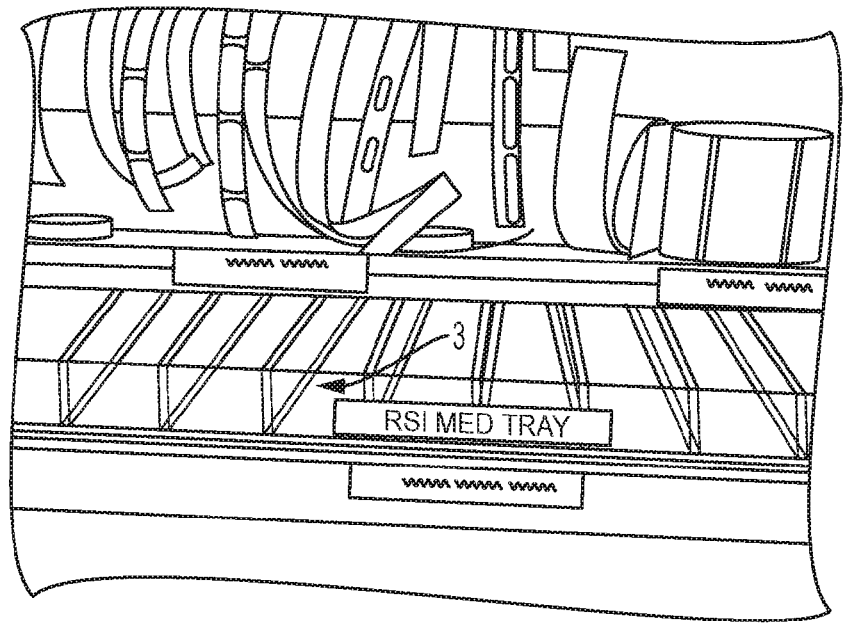
FIG. 4 is a photograph of the side view of a rapid sequence intubation tray (RSI MED TRAY) stored on a shelf and a plurality of medication labels stored on another shelf.

In some embodiments, the label sections 10 aligned with the parallel compartments 3 are divided into subsections 12. In preferred embodiments, each label section 10 contains the entirety of indications 13 needed for an emergency care provider to administer the specific medication indicated in the label section 10. In preferred embodiments and as illustrated in FIG. 3, the indications of medication name, concentration, and volume to be administered are also displayed on small labels 14 that are suitably attached to the medication-containing receptacles. The small labels can be stored in label rolls in close physical proximity to the rapid sequence medical procedure tray(s) as illustrated in FIG. 4.

In some embodiments, one subsection 12 of a label section contains a medication name, a second subsection 12 of a label section 10 contains a medication concentration, and a third subsection 12 of a label section 10 contains the medication volume to be administered to the patient. The skilled artisan can appreciate that any label section 10 can be divided into a plurality of subsections 12 and can contain a plurality of indications 13 related to the medication contained in receptacles located in the parallel compartment 3. The skilled artisan can further appreciate that the exact alignment of the label sections 10 and their respective subsections 12 with each other and the parallel compartment 3 is crucial for the functionality of the subject invention.

In preferred embodiments, the label subsections containing medication name indications 13 are located directly above the label subsections containing the medication concentration and medication volume indications 12. In alternative embodiments, the information contained in label sections 10 and subsections 12 can be arranged in any order.

In most embodiments, the indications 13 of the label sections 10 and subsections 12 are in white or light color on black or dark background or, alternatively, in black or dark color on white or light background. In many embodiments, the fonts of the medication name indication and medication volume indication are larger than the fonts of the medication concentration indication or any additional indications displayed on the label section 10 or subsection 12. The skilled artisan can appreciate that the indications of information critical for the rapid sequence administration of medications to a patient in an emergency situation, such as medication name and volume to be administered, is most prominently displayed on the label sections 10, label subsections 12, and small labels 14 to ensure error-free information transfer.

In some embodiments, the medication name, concentration, and volume indications 13 in the label sections 10 and subsections 12 are displayed in colors or fonts different from the patient weight 8 and purpose or use indications 9. In alternative embodiments, the medication name, concentration, and volume indications 13 are displayed in colors and fonts similar to the patient weight 8 and purpose or use indications 9.

In further embodiments, the names, concentrations, and volumes of one group of medications are displayed in colors or fonts different from the names, concentrations, and volumes of another group of medications. In alternative embodiments, all names, concentrations, and volumes of some medications are displayed in similar colors or fonts.

In some embodiments of the subject invention, the backgrounds of label sections 10 and subsections 12 are colored in a single color. In other embodiments, the backgrounds of label sections 10 and subsections 12 are colored in different colors. In certain embodiments, the background colors are used to indicate groups of label sections 10. In some embodiments, backgrounds of label sections 10 indicating medications used to elicit similar clinical effects which medications can be used as alternatives to each other, are colored in a single color. In other embodiments, backgrounds of label sections 10 of medications to be administered in sequence are colored in a single color. For example, the medication on a first label section 10 located on the left side of a sequence of same-colored-background label sections 10 is administered first, followed by the medication located on the label section 10 to the right of said first label section 10 and so on. In yet other embodiments, backgrounds of label sections 10 of medications used during a specific phase of a procedure, for example during the early or induction phase of anesthesia, are colored in a single color. The person with ordinary skill in the art will be able to recognize numerous other modes of color coding that would be applicable to devices and methods of the subject invention, which modes of color coding are within the scope of the subject invention.

In most embodiments of the subject invention, the volume indications displayed on each label section 10 or subsection 12 are calculated based on the specific patient weight indication 8 displayed on the label 7. In preferred embodiments, the patient weight indication 8 is located above the label sections 10. In alternative embodiments, the patient weight indication 8 can be located in any location on the label 7, as long as it is displayed in a manner readily observable upon inspection of the label 7.

In most embodiments and as illustrated in FIG. 2, the subject invention comprises a plurality of labels 7 each of which contains a single patient weight indication 8, wherein the medication volumes displayed on said label 7 are calculated based on the single patient weight indication 8. In preferred embodiments, the emergency care provider can rapidly select the label 7 with the patient weight indication 8 that matches the weight of the patient to be treated, place the label 7 into the single large compartment 5 of a tray loaded with medications receptacles pre-apportioned according to the patient weight indication on the label and administer the volumes indicated on the label sections 10 or subsections 12 aligned with the parallel compartments 3 holding the medication receptacles. The ready availability of pre-apportioned medications in combination with the pre-calculated, patient weight-based volumes and display of patient weight indication and weight-based volumes on a single label provide for rapid, accurate and patient-tailored medication during emergency treatments.

In preferred embodiments, the medications in the receptacles are pre-apportioned at concentrations that enable the use of more than one label in a respective tray. The skilled artisan can appreciate that with increasing body weight the amount of medication needed for a patient to elicit a clinical effect normally increases. The skilled artisan can further appreciate that a medication can be prepared at a higher concentration in order to reduce the volume of medication to be administered. In preferred embodiments of the subject invention, the pre-apportioned concentrations of medications in receptacles of a tray are calculated to allow the use of more than one label with said tray, with each alternative label indicating volumes of medications, which volumes fall within a range of volumes that can be safely applied to patients of the body weight indicated on the respective label. For example, a tray of the subject invention can contain receptacles with pre-apportioned medications at concentrations that allow the interchangeable use of a plurality of labels with said tray, because the increased volumes required for patients with higher body weights are within a range of volumes that can be safely administered to patients of the respective weights. In a preferred embodiment, the pluralities of labels that can be used with a single tray are of one color to indicate their interchangeability. In alternative embodiments, a plurality of trays are prepared with each tray containing medication receptacles of different medication concentrations, where each tray has to be used with a single label only.

In some embodiments of the subject invention, the labels are color-coded according to the procedure, purpose or use of the tray. In preferred embodiments, similar medications are used for a single procedure. In alternative embodiments, different medications are used for a single procedure. In some embodiments, the medications used in a single procedure can be different, and the labels indicating a first group of medications to be used for said procedure are of one first color and the labels indicating a second or third group of medications to be used for said procedure are of one second or third color, respectively.

In preferred embodiments, the colors used to identify groups of labels to be used with a single tray are different from the colors used to identify groups of medications to be used for the performance of a single procedure. The skilled artisan can appreciate that the distinctiveness of the color coding system is an integral function of the subject invention to reduce the risk of confusion of the emergency care provider as to the combination of tray and label to use for a patient of a specified weight to perform a specified procedure.

In further embodiments, the subject invention contains as many labels as necessary to cover the weight range from prematurely born babies to adults. The skilled artisan can appreciate that the weight ranges are smaller at low weights and larger at higher weights. For example, the weight range between 0.5 kg and 5 kg can be covered by 0.25 to 0.5 kg increments, whereas the weight range between 65 and 70 kg can be covered by 2.5 to 5 kg increments.

Figure 5:
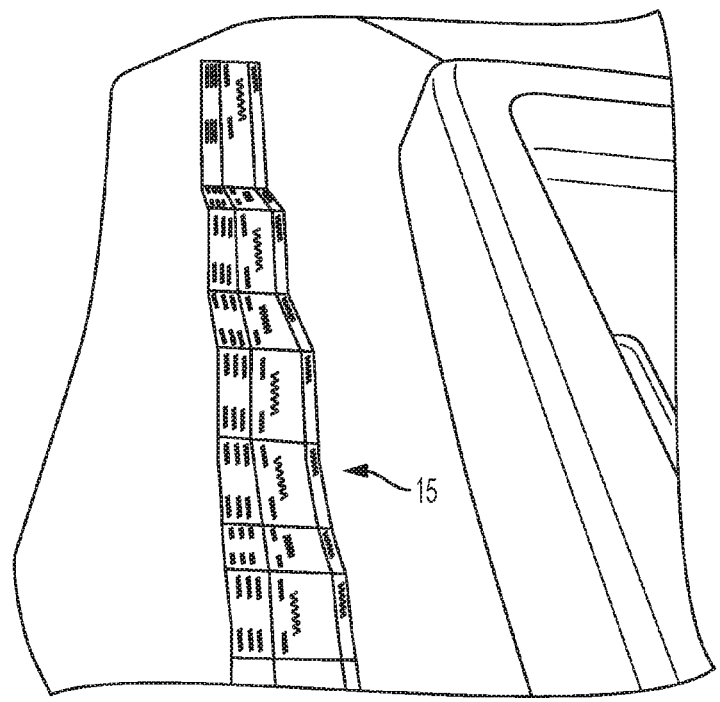
FIG. 5 is a photograph of a plurality of color-coded labels of medication name, concentration, and dosage indications.
Figure 6:
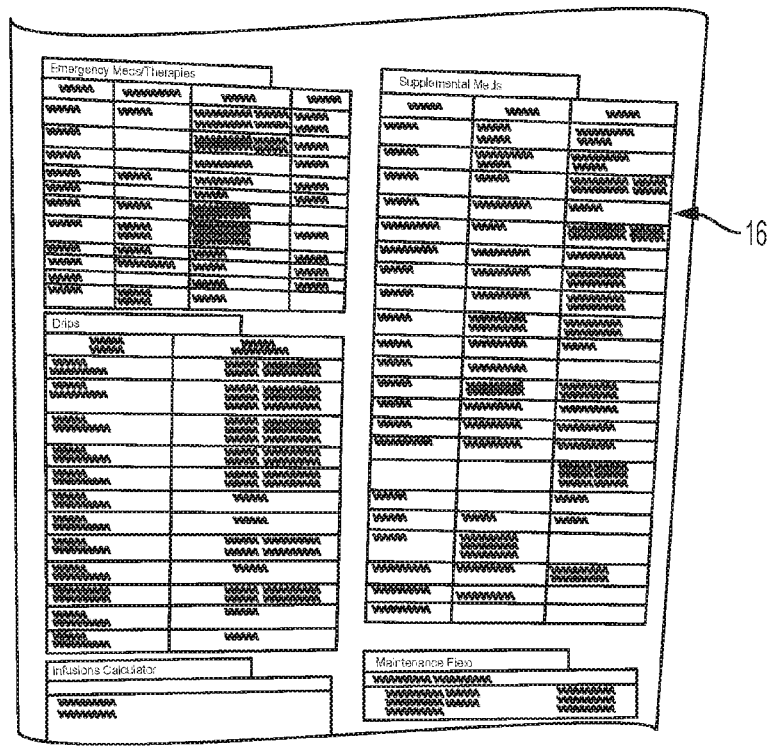
FIG. 6 is a photograph of a wall-mounted list of emergency medications/therapeutics, supplemental medications, infusion liquids, maintenance fluids and an infusion calculator.

In some embodiments illustrated in FIG. 5, the subject invention provides for additional color coded labels 15, which correspond in their color coding to the labels 7 to be placed into the single large compartment 5 of the tray. In preferred embodiments, the additional color coded labels 15 contain indications of any information relevant to the administration of medications indicated on the labels 7 to be put into the trays 1 of the subject invention, which information can include, but is not limited to, medication dosages, medication side effects, medication interactions, clinical tests to be administered to monitor medication effects, and contraindications to the administration of said medications.

In some embodiments, the subject invention provides for additional indications to be wall-mounted 16, which additional indications provide, for example, an infusion calculator and lists of additional medications to be supplied to a patient during or after an emergency procedure, including, but not limited to, supplemental medications, infusion liquids, and maintenance fluids.

In some embodiments of the subject invention, the receptacles containing the pre-apportioned medication volumes are syringes containing an injectable liquid form of the medication. In most embodiments, the receptacles containing pre-apportioned medication volumes are marked with individual small labels 14, as illustrated in FIG. 4, which small labels 14 indicate the medication name and medication concentration. The small labels can be conveniently stored on label rolls located in close proximity to the rapid sequence procedure trays.

While the subject invention describes a use of the subject invention in endotracheal intubation, other uses and modifications apparent to a person skilled in the art and having benefit of the subject disclosure are contemplated to be within the scope of the subject invention.

METHODS AND MATERIALS

Example 1

A rapid sequence intubation tray is provided that comprises labels with a first group of backgrounds of a first color for sections indicating medications for use as fast-acting anesthetic agents, a second group of backgrounds of a second color for sections indicating medications for use as fast-acting neuromuscular blocking agents, and a third group of backgrounds of a third color for sections indicating auxiliary medications for use as parasympathetic blockers or cough reflex suppressants. The colors of the first group of backgrounds differ on every label and alert the emergency care provider to the differences in volumes on each label based on the different weights assigned to each label. In contrast, the colors of the second group of backgrounds are similar on some labels indicating similar volumes of medications of the second group for a range of patient weights. The colors of the third group of backgrounds are similar on a large number of labels indicating a "standard dose" of auxiliary medications for a wide range of patient weights.

Example 2

Color-coded labels are provided that are used in conjunction with the labels positioned into the single large tray compartments, which additional labels can be placed in close proximity to the tray for ease of use. The additional labels comprise sections, which sections match in color to same-colored sections of the single label in the single large tray compartment. The additional labels serve as indications of additional information concerning the medications indicated on same-colored single label in the single large tray compartment. For example, the information displayed on the additional labels can relate to medication interactions, medication side effects, antidote medications or lists of supplemental medications and therapies, including infusion liquids and volumes of maintenance fluids.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A device to reduce medication error in rapid sequence medication administration during urgent medical procedures, the device comprising:
    a tray having a plurality of parallel compartments holding medication receptacles and a single compartment perpendicular to the plurality of parallel compartments, wherein the single compartment comprises:
    a label covering a surface of the single perpendicular compartment and displaying a patient weight and a purpose of use, wherein the label comprises sections suitably aligned with a single parallel compartment; and
    a plurality of indications displayed on the label, wherein the indications comprise a medication name and a medication volume, wherein the medication volume is calculated based on the patient weight indication displayed on said label.

2. The device according to claim 1, wherein each parallel compartment holds a plurality of medication receptacles.

3. The device according to claim 1, wherein the medication receptacles are syringes.

4. The device according to claim 1, wherein the medication receptacles comprise the volume indicated on the label aligned with a parallel compartment of the plurality of parallel compartments holding the medication receptacles.

5. The device according to claim 2, wherein each medication receptacle contains the exact volume indicated on the label aligned with a parallel compartment of the plurality of parallel compartments holding the medication receptacles.

6. The device according to claim 1, comprising a plurality of labels, each label having a different weight indication, wherein the entirety of medication volume indications on said label are calculated based on the weight indication of said label.

7. The device according to claim 1, wherein the medication name indications comprise generic names and/or a plurality of proprietary names commonly used for the medications.

8. The device according to claim 6, further comprising a color code, wherein the background of each label is of a different color.

9. The device according to claim 1, further comprising a color code, wherein the backgrounds of a group of label sections are of a single color.

10. The device according to claim 9, wherein the group of label sections with same-colored backgrounds indicates a group of medications that can be given alternatively to affect a similar response in the patient.

11. The device according to claim 9, wherein the group of label sections with same-colored backgrounds indicates a group of medications given within a specified time period.

12. The device according to claim 9, wherein the group of label sections with same-colored backgrounds indicates a group of medications given in rapid succession.

13. The device according to claim 1, further comprising a plurality of small labels and indications, wherein the indications on each small label match the indications on one section of the single large label, and wherein each small label is attached to one medication receptacle contained in the parallel compartment aligned with the one section of the single large label.

14. The device according to claim 1, further comprising a plurality of additional labels, wherein the color of each section of the additional label matches the color of a section of the single label to be put into the single large compartment of the tray and each section of the additional label comprises an indication of information related to the medication indicated on the same-colored section of the single large label to be put into the tray.

15. The device according to claim 1, wherein the label further comprises subsections.

16. The device according to claim 1, wherein the indications further comprise a medication concentration.

* * * * *